(12) United States Patent
Katsuhara et al.

(10) Patent No.: US 8,372,476 B2
(45) Date of Patent: Feb. 12, 2013

(54) METHOD OF PLASMONIC CRYSTAL

(75) Inventors: Tomoko Katsuhara, Kanagawa (JP);
Yuuki Watanabe, Kanagawa (JP);
Hajime Matsumura, Tokyo (JP)

(73) Assignee: Sony Corporation, Tokyo (JP)

( * ) Notice: Subject to any disclaimer, the term of this patent is extended or adjusted under 35 U.S.C. 154(b) by 804 days.

(21) Appl. No.: 12/538,936

(22) Filed: Aug. 11, 2009

(65) Prior Publication Data
US 2009/0297693 A1 Dec. 3, 2009

(30) Foreign Application Priority Data

May 2, 2007 (JP) .................................. 2007-121439
Aug. 11, 2008 (JP) .................................. 2008-206841

(51) Int. Cl.
*B05D 5/06* (2006.01)
(52) U.S. Cl. ............. 427/162; 427/8; 356/445; 356/301
(58) Field of Classification Search .................. 427/162; 356/445, 301
See application file for complete search history.

(56) References Cited

U.S. PATENT DOCUMENTS

| | | | |
|---|---|---|---|
| 5,164,589 A | 11/1992 | Sjodin | |
| 7,483,130 B2 * | 1/2009 | Baumberg et al. | 356/301 |
| 7,773,228 B1 * | 8/2010 | Hollingsworth et al. | 356/445 |
| 2002/0021445 A1 * | 2/2002 | Bozhevolnyi et al. | 356/445 |
| 2006/0119853 A1 * | 6/2006 | Baumberg et al. | 356/445 |
| 2006/0257090 A1 * | 11/2006 | Podolskiy et al. | 385/129 |
| 2009/0045351 A1 * | 2/2009 | Smolyaninov et al. | 250/458.1 |
| 2009/0273779 A1 * | 11/2009 | Baumberg et al. | 356/301 |
| 2009/0297693 A1 * | 12/2009 | Katsuhara et al. | 427/8 |
| 2011/0109854 A1 * | 5/2011 | Tang et al. | 349/117 |
| 2011/0285942 A1 * | 11/2011 | Guo et al. | 349/96 |
| 2012/0050732 A1 * | 3/2012 | Lu et al. | 356/301 |

FOREIGN PATENT DOCUMENTS

| | | |
|---|---|---|
| JP | 04-501462 | 3/1992 |
| JP | 2008-175616 | 7/2006 |
| JP | 2008-014732 | 1/2008 |
| JP | 2008-519254 | 6/2008 |
| WO | 2005-029164 | 3/2005 |

OTHER PUBLICATIONS

"Towards Plasomnic Band Gap Laser," Article, published by Applied Physics Letters, 2004, vol. 85, pp. 3968-3970.
Japanese Office Action for corresponding JP2008-206841 issued on May 18, 2010.

* cited by examiner

*Primary Examiner* — Khanh P Nguyen
*Assistant Examiner* — Margaret Squalls
(74) *Attorney, Agent, or Firm* — K&L Gates LLP (57) ABSTRACT

A method of designing a plasmonic crystal is provided. The method includes: determining an arrangement period of a plasmonic crystal formed on a metal surface at an interface between a dielectric and the metal in accordance with a dispersion relation of a surface plasmon polariton at the interface and a Bragg reflection condition of the surface plasmon polariton.

10 Claims, 7 Drawing Sheets

$$\Lambda = \frac{k_{spp}}{2}$$

METHOD OF PLASMONIC CRYSTAL

CROSS REFERENCES TO RELATED APPLICATIONS

The present application claims priority to Japanese Priority Patent Applications JP 2007-121439 and JP 2008-206841 filed in the Japan Patent Office on May 2, 2007 and Aug. 11, 2008, respectively, the entire contents of which is hereby incorporated by reference.

BACKGROUND

The present disclosure relates to a design method of a plasmonic crystal. Particularly, the present disclosure relates to a design method of the plasmonic crystal capable of generating a plasmonic band gap in optional energy by determining an arrangement period of the plasmonic crystal under given conditions.

A Surface Plasmon Polariton or SPP is a compressional wave of electrons existing at an interface between a metal and a dielectric, which is a surface electromagnetic wave propagating at the metal-dielectric interface. In the case that there is a periodic lattice structure on a metal surface of the metal-dielectric interface, the SPP is Bragg-reflected by the lattice in a certain wavelength and is propagated in the opposite direction to generate a standing wave. The lattice structure is referred to as a concavo-convex structure or a relief structure.

In the SPP which becomes the standing wave, electric fields are localized at anti-nodes thereof. The SPP which has become the standing wave generates two different energy states by relative phases with respect to the lattice. As a result, an energy gap referred to as a plasmonic band gap appears at a dispersion curve of the SPP.

The periodic relief structure on the metal surface which generates the plasmonic band gap is referred to as a plasmonic crystal. The plasmonic crystal has been researched from the basics to the applications because the control of a radiation field or enormous enhancement of the electric field can be expected. In "Applied Physics Letters, 2004, Vol. 85, p 3968-3970" (Non-patent document 1), an approach for enhancing light emitting intensity of dye by depositing dye thin films on a plasmonic crystal is reported. The enhancement technology in the emitting of dye using localization and enhancement of the electric field at a plasmomic band gap end (hereinafter, referred to as a merely gap end) is referred to as a plasmonic band gap laser. It is expected that the plasmonic band gap laser leads to development of an organic EL element and the like which can obtain high light emitting efficiency.

On the other hand, a sensor utilizing the SPP is used for detecting interaction among various materials in recent years. The sensor is referred to as a surface plasmon resonance (SPR) sensor.

When polarized light is incident on the metal-dielectric interface under the total reflection condition in order to excite the SPP, a bleeding component which is called an evanescent wave is generated at the interface. In the total reflection condition, energy of incident light will normally be energy of reflection light almost without loss. However, under a wavenumber matching condition in which the evanescent wave corresponds to the wavenumber of the SPP, energy of incident light is used for excitation of the SPP and the SPR is generated, which reduces energy of reflected light. The energy change of reflected light can be detected as change of wavenumber of reflected light with respect to incident light.

Since the wavenumber matching condition depends on an incident angle θ of incident light, when the wavenumber of reflected light is detected while changing the incident angle θ, the SPR is generated at a certain angle and the change of wavenumber will be the maximum. This angle is called resonance angle θsp, and the wavenumber of reflected light at the resonance angle θsp is called a peak wavenumber (or absorption peak).

Since the resonance angel θsp depends on permittivity of a dielectric, change of the resonance angle θsp and the peak wavenumber (hereinafter, referred to as a shift) corresponds to change of the permittivity of the dielectric. Therefore, the shift of the peak wavenumber is detected by using a sample including various materials as dielectrics, thereby detecting permittivity change of the sample caused by the interaction among materials.

In the SPR sensor, the interaction among materials in the sample is detected by the change of permittivity, therefore, it is not necessary to label materials by radioactive materials, fluorescent materials and the like, which enables sensitive detection. Accordingly, the SPR sensor is suitably used particularly as a bio sensor which evaluates the interaction of biological materials such as protein or nucleic acid. In Japanese Patent No. 3294605 (Patent Document 1), the SPR sensor as an optical bio-sensor device is disclosed.

In the SPR sensor, the change of permittivity of the sample, that is, the interaction among materials in the sample is detected by detecting the shift of the peak wavenumber. However, when detecting the interaction among materials whose molecular masses are extremely small or extremely minute amounts of materials, the shift of the peak number is less than a detection limit because the change of permittivity is small, as a result, it is sometimes difficult to obtain sufficient measurement sensitivity.

Thus, it is desirable to provide a design method of a plasmonic crystal which can be a basic technology for allowing the SPR sensor to be highly sensitive.

SUMMARY

According to an embodiment, there is provided a design method of a plasmonic crystal in which an arrangement period of a plasmonic crystal formed on a metal surface at an interface between a dielectric and a metal is determined in accordance with a dispersion relation of a surface plasmon polariton at the interface and a Bragg reflection condition of the surface plasmon polariton shown in a following formula (1):

$$2 \times k_{spp} = \frac{2\pi}{\Lambda} \quad (1)$$

wherein $K_{spp}$ is a wavenumber of the surface plasmon polariton (SPP), and $\Lambda$: is the arrangement period.

In the design method, the arrangement period is determined in accordance with the dispersion relation and the Bragg reflection condition under an optional incident-light frequency condition and a dielectric permittivity condition, thereby obtaining a plasmonic crystal having a plasmonic band gap end in a frequency corresponding to an incident light frequency. At this time, it is preferable that a surface plasmon resonance Kretschmann configuration including a dielectric, a metal and a prism is applied.

The design method can be applied for allowing the surface plasmon resonance sensor to be highly sensitive by forming the obtained plasmonic crystal on the metal surface at an interface between a sample and the metal in the surface plasmon resonance sensor. The design method can be also applied for increasing the light emitting intensity of dye by depositing dye thin films on the obtained plasmonic crystal.

In the embodiment, the plasmonic band gap means an energy gap appearing in a dispersion curve of the SPP at the dielectric/metal interface to which the plasmon crystal is arranged, and the plasmonic band gap end means a high energy-side end (upper end) and/or a low energy-side end (lower end) in the plasmonic band gap.

The arrangement period of the plasmonic crystal is determined under given conditions, thereby providing the design method of the plasmonic crystal capable of generating a plasmonic band gap in optional energy.

Additional features and advantages are described herein, and will be apparent from the following Detailed Description and the figures.

BRIEF DESCRIPTION OF THE FIGURES

FIG. 9A to FIG. 9D show the SPP dispersion relations of the plasmonic crystals in which the relief structures having arrangement periods 280, 300, 320 and 340 nm are formed;

DETAILED DESCRIPTION

In a SPR sensor, the permittivity change of the sample is detected by detecting a shift of the peak wavenumber. Therefore, when a fixed permittivity change is detected, the more strongly the shift of the peak wavenumber due to the permittivity change appears, the higher the detection sensitivity of the permittivity change becomes.

Accordingly, with regard to the above plasmonic band gap, considering that the shift of the peak wavenumber with respect to the fixed permittivity change is increased by using the change of the gradient at a gap end in a dispersion curve of the SPP.

Figure 1:
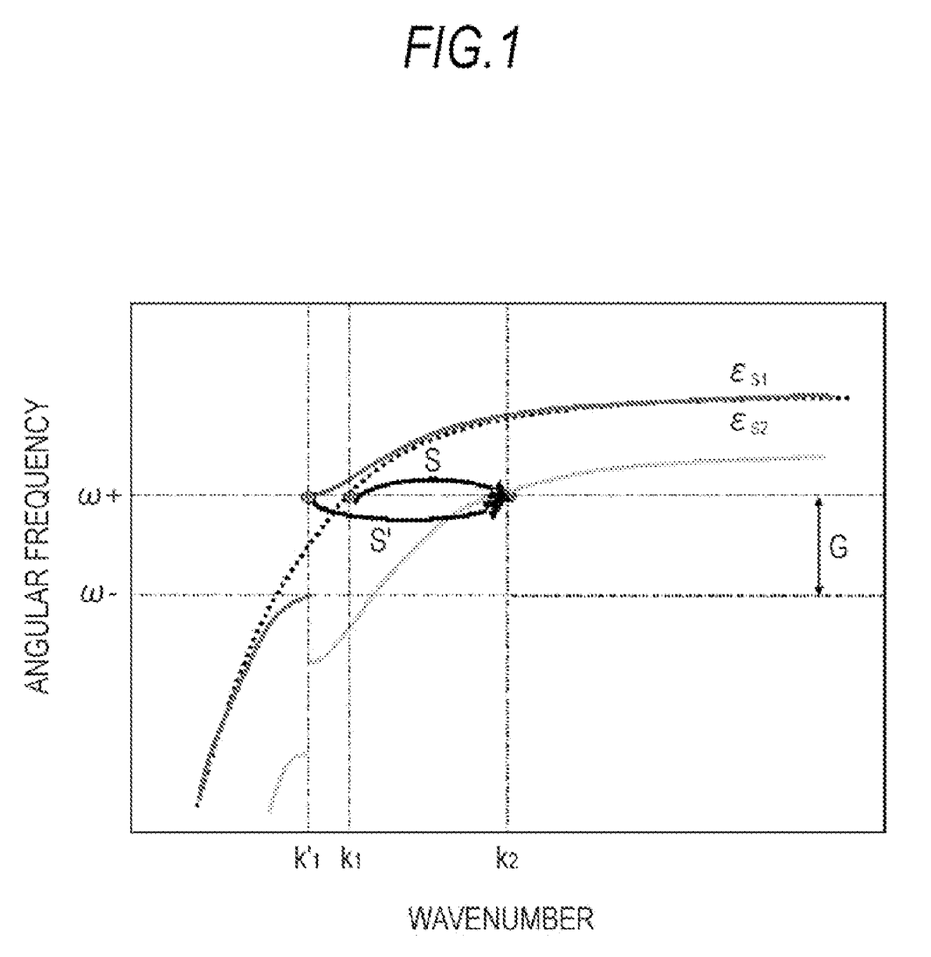
FIG. 1 is a graph for explaining a concept of supersensitization of a SPR sensor using a plasmonic band gap.

FIG. 1 is a graph for explaining a concept of supersensitization of the SPR sensor using the plasmonic band gap. The graph shows, in the SPR sensor, the shift of the peak wavenumber when permittivity of a dielectric changes from $\in_{s1}$ to $\in_{s2}$. In the drawing, a symbol "G" denotes the plasmonic band gap.

When the permittivity of the dielectric is $\in_{s1}$, the peak wavenumber in the case that the plasmonic crystal is arranged on the metal surface at the interface between the metal and the dielectric is indicated by a solid line, and the peak wavenumber in the case that there is no plasmonic crystal is indicated by a dotted line. When a frequency of incident light is made to correspond to an angular frequency ω+ at the gap end (upper end of the high energy side), a peak wavenumber $k'_1$ in the case that the plasmonic crystal is arranged appears at a low-frequency side as compared with a peak wavenumber $k_1$ in the case that there is no plasmonic crystal. That is to say, $k'_1$ is smaller than $k_1$.

In the case that the permittivity of the dielectric is changed to $\in_{s2}$, when the peak wavenumber in the incident light of the same frequency is $k_2$, a shift "S" of the peak wavenumber in the case that the plasmonic crystal is arranged will be "$k_2-k'_1$". A shift "S" of the peak wavenumber in the case that there is no plasmonic crystal will be "$k_2-k_1$".

Since $k'_1$ is smaller than $k_1$, "$k_2-k'_1$," is larger than "$k_2-k_1$", and the relation between the shift S' ($k_2-k'_1$) of the peak wavenumber when in the case that the plasmonic crystal is arranged and the shift S ($k_2-k_1$) in the case that there is no plasmonic crystal will be S'>S. That is, the plasmonic crystal is arranged at the interface with respect to the dielectric, thereby increasing the shift of the peak wavenumber due to the permittivity change of the dielectric from $\in_{s1}$ to $\in_{s2}$.

As described above, it is possible to detect the shift of the peak wavenumber with respect to the fixed permittivity change to be larger and to increase the detection sensitivity of the permittivity change by arranging the plasmonic crystal at the interface with respect to the dielectric and detecting the shift of the peak wavenumber by using incident light having the frequency of the gap end.

However, in order to perform such highly sensitive detection in a normal SPR sensor, it is necessary to previously form the plasmonic crystal in which the frequency of the gap end corresponds to the frequency of incident light provided at the sensor to be arranged on the metal surface.

The present inventors, after making a study for forming the plasmonic crystal having the gap-end frequency corresponding to an optional incident-light frequency, have found prescribed conditions which can obtain such plasmonic crystal, and have completed the design method of the plasmonic crystal according to an embodiment. That is, the present inventors have clarified that the plasmomic crystal having the plasmonic gap end in the frequency which corresponds to the optional incident-light frequency by determining the arrangement period of the plasmonic crystal in accordance with the dispersion relation of the SPP at the interface between the dielectric and the metal as well as a Bragg reflection condition of the SPP shown the following formula (1):

$$2 \times k_{spp} = \frac{2\pi}{\Lambda} \quad (1)$$

wherein $K_{spp}$ is a wavenumber of the surface plasmon polariton (SPP), and $\Lambda$: is the arrangement period.

In the design method of the plasmonic crystal, it is possible to obtain the plasmonic crystal having the plasmonic band gap end in the frequency which corresponds to the incident-light frequency by determining the arrangement period in accordance with the SPP dispersion relation and the Bragg reflection condition under the optional incident-light frequency condition and the dielectric permittivity condition.

Hereinafter, an embodiment will be explained with reference to the drawings, citing the surface plasmon resonance Kretschmann configuration which is generally used for excitation of the SPP as an example. The embodiment explained below shows one typical example and is limited thereby.

Figure 2:
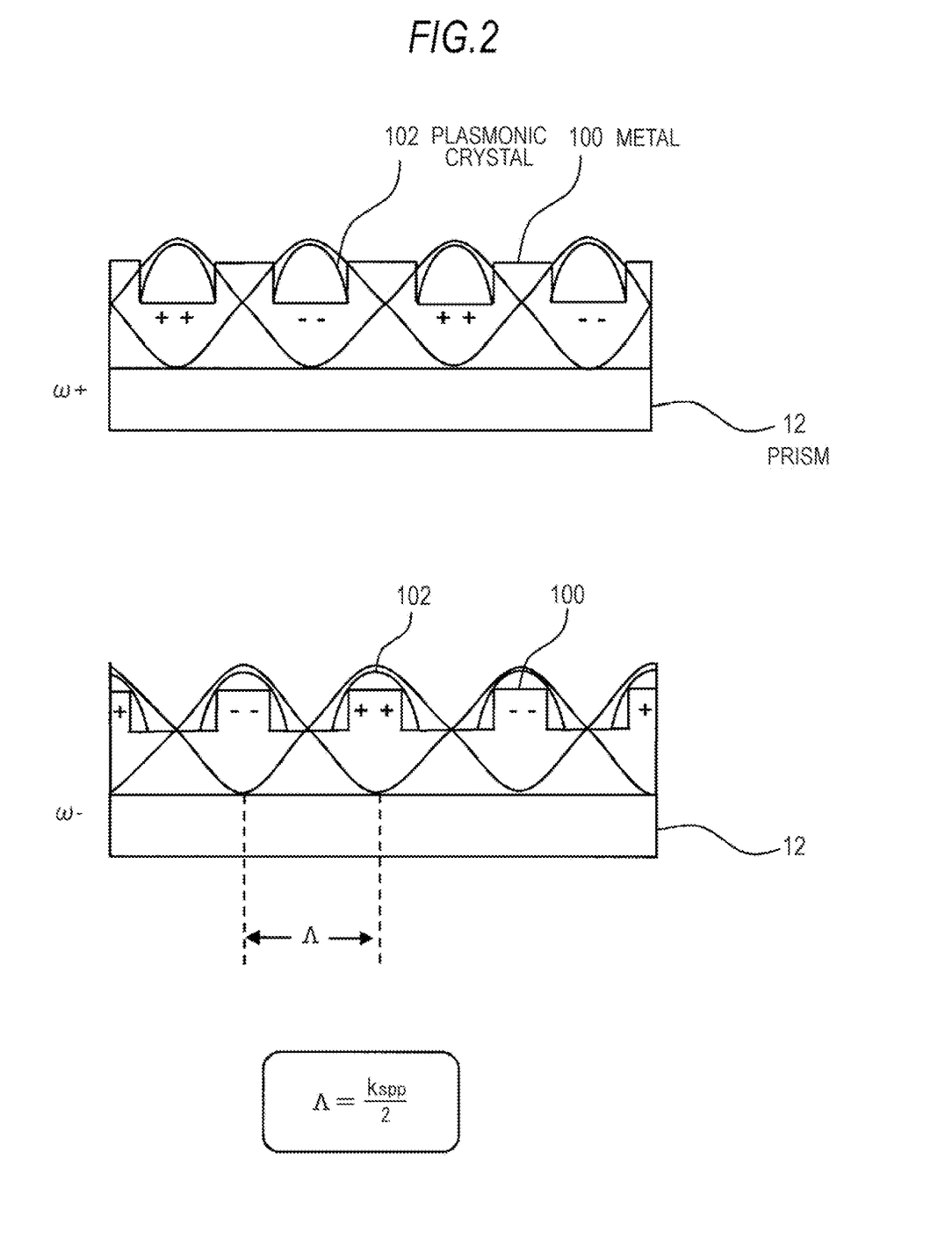
FIG. 2 a schematic view for explaining an arrangement period of a plasmonic crystal in a design method according to the embodiment.

FIG. 2 is a schematic view for explaining an arrangement period of the plasmonic crystal in the design method according to the embodiment. The surface plasmon resonance Kretschmann configuration includes a dielectric, a metal and a prism. In FIG. 2, a numeral 12 denotes a prism, a numeral 100 denotes a metal and a numeral 102 denotes a prasmonic crystal formed on the metal surface of the dielectric side.

In FIG. 2, a sign $\Lambda$ shows an arrangement period of a relief in a periodic relief structure included in the plasmonic crystal 102. When the arrangement period $\Lambda$ satisfies given conditions, the SPP generates a standing wave, and an electric field is localized at an anti-node thereof.

The SPP which has became the standing wave can take two energy states which are angular frequencies $\omega+$ and $\omega-$ as shown in an upper row and a lower row in FIG. 2. Accordingly, the plasmonic band gap having the angular frequencies $\omega+$ and $\omega-$ as upper and lower ends in the gap is generated in the dispersion curve of the SPP (refer to FIG. 1).

When the plasmonic band gap is generated, the SPP having the frequency in the gap is prohibited from propagating. At the gap end, the gradient of the dispersion curve ($d\omega/dk$) becomes "0" as well as group velocity becomes "0", as a result, the electric field is largely enhanced because the SPP is shut up.

At this time, the arrangement period $\Lambda$ is formed so as to satisfy the SPP dispersion relation at the interface between the dielectric and the metal 100 as well as the Bragg reflection condition of the SPP, thereby allowing the frequency of incident light to correspond to the angular frequency $\omega+$ at the upper end of the gap. That is, in an optional incident-light frequency condition and the dielectric permittivity condition, the plasmonic crystal having the gap end (upper end) in the frequency which corresponds to the incident light frequency.

Subsequently, a specific procedure of the design method of the prasmonic crystal according to the embodiment will be explained.

First, the SPP dispersion relation is calculated in the given incident-light frequency condition and the dielectric permittivity condition. The reflection light intensity in a three-layer system of dielectric/metal/prism is calculated by using Fresnel equations and equations of multiple wave interference, and a SPR curve in the optional incident light wavelength and dielectric conditions is calculated. Then, the angle of a dip is plotted in the incident light wavelength to obtain the dispersion relation of the SPP.

Next, the Bragg reflection condition of the SPP is calculated in the given incident light frequency condition. The Bragg reflection condition is shown by the following formula (1). Here, "kspp" indicates the wavenumber of the SPP, which is the same as the wavenumber of the dielectric/metal interface.

$$2 \times k_{spp} = \frac{2\pi}{\Lambda} \quad (1)$$

$K_{spp}$: Wavenumber of Surface plasmon polariton (SPP)
$\Lambda$: Arrangement period Accordingly, the SPP dispersion relation and the Bragg reflection condition which should be satisfied by the arrangement period $\Lambda$ can be obtained. The arrangement period $\Lambda$ which satisfies them under the optional incident-light frequency condition and the dielectric permittivity condition is calculated, thereby obtaining the prasmonic crystal having the gap end (upper end) in the frequency corresponding to the incident light frequency.

Accordingly, for example, the plasmonic crystal having the gap end in the frequency corresponding to the frequency of incident light provided at the SPR sensor is previously designed and is formed on the metal surface of the interface between the sample and the metal of the sensor to thereby detect the shift of the peak wavenumber with respect to a fixed permittivity change to be larger and to increase the detection sensitivity of the permittivity change.

Generally, the SPR sensor improves the sensitivity as the wavelength of incident light becomes long. In the design method of the plasmonic crystal according to the embodiment, the arrangement period of the plasmonic crystal is determined so as to correspond to incident light of the wavelength, thereby further improving the sensitivity of the sensor. It is not necessary that the frequency of the gap end of the plasmonic crystal exactly corresponds to the frequency of incident light of the SPR sensor, and it is possible to increase the sensitivity of the sensor by using the plasmonic crystal in which incident light has higher energy than the gap end.

Furthermore, the design method of the plasmonic crystal according to the embodiment can be not only applied for increasing the sensitivity of the SPR sensor but also applied to various applications by using localized and enhanced energy for the purpose of exciting various material efficiently or promoting reaction between materials. That is, in the design method of the plasmonic crystal according to the embodiment of the invention, the arrangement period of the plasmon crystal is determined based on given conditions, thereby generating the plasmonic band gap in optional energy (frequency) as well as localizing and increasing the energy. Therefore, the design method can be applied for, for example, exciting dye thin films deposited on the plasmonic crystal efficiently and increasing the light emitting intensity of dye by using specific energy which have been localized and enhanced. Additionally, for example, the design method can be also used for promoting reaction of a photoresist on the plasmonic crystal and increasing drawing accuracy of a resist by using the specified frequency which have been localized and enhanced.

EXAMPLES

Example 1

1. Prediction of an Arrangement Period in a Plasmonic Crystal

In the Kretschmann configuration (refer to Journal of Applied Physics, Vol. 79, p. 7383-7385) in which the SPP is allowed to coupled by using a prism, a system which satisfies both a condition in which the SPR is generated (SPP dispersion relation) and a condition in which the SPP and the plasmonic crystal are coupled (Bragg reflection condition) was estimated.

As a metal thin film, a plasmonic crystal was used, in which the periodic relief structure was formed on a Au 45 nm/Bk7 substrate. As a surface dielectric layer, air (n=1) or purified water (n=1.33) was used.

Figure 3:
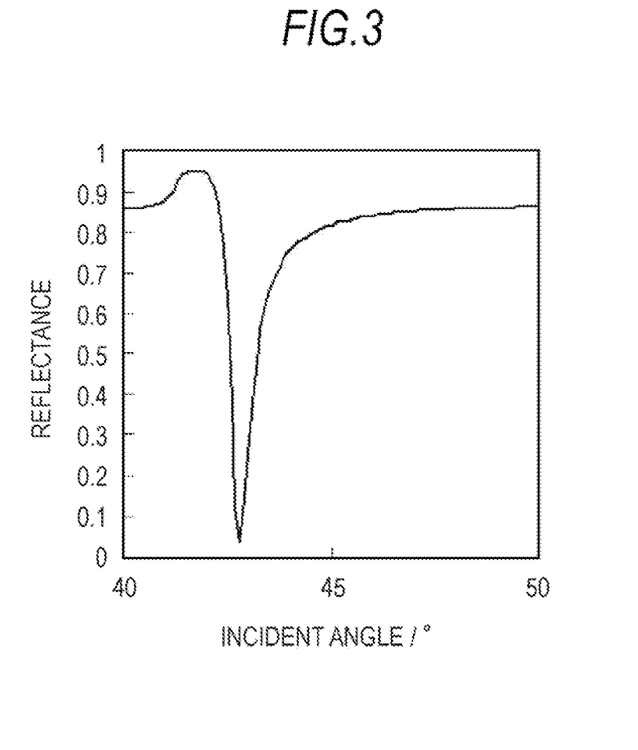
FIG. 3 is a graph showing a SPR curve calculated by using Fresnel equations and equations of multiple wave interference when the incident light wavelength is 770 nm and a surface refraction index is "1" in a three-layer system of surface dielectric layer/metal thin film/prism.

The reflection light intensity in the three-layer system of surface dielectric layer/metal thin film/prism was calculated by using Fresnel equations and equations of multiple wave interference to find a SPR curve in the optional incident-light wavelength and the permittivity condition (refer to "Bunseki" by Kazuyoshi Kurihara et al, No. 4, 2002, p. 161-167). FIG. 3 shows the SPR curve when the incident light wavelength is 770 nm and a surface refraction index is "1"). The angle of the dip was plotted in the incident light wavelength to obtain the dispersion relation of the SPP.

On the other hand, the Bragg reflection condition of the SPP in an optional crystal is given by the following formula (1):

$$2 \times k_{spp} = \frac{2\pi}{\Lambda} \quad (1)$$

wherein $K_{spp}$ is a wavenumber of the surface plasmon polariton (SPP), and $\Lambda$ is the arrangement period.

Figure 4:
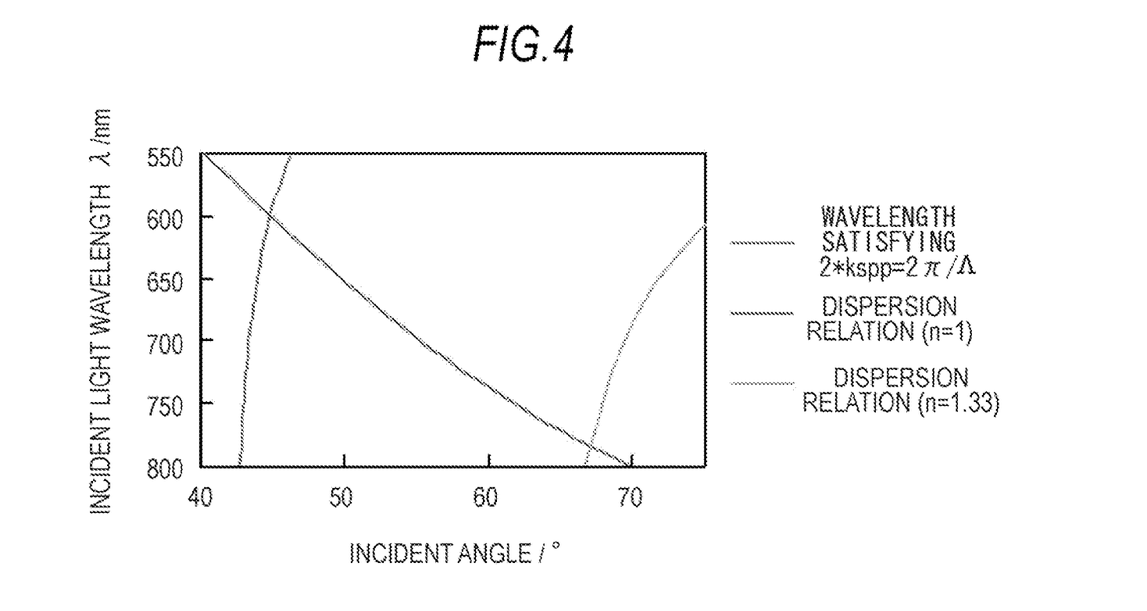
FIG. 4 is a graph showing a SPP dispersion relation and the Bragg reflection condition in the case that the arrangement period of a relief structure of the plasmonic crystal is 280 nm.
Figure 5:
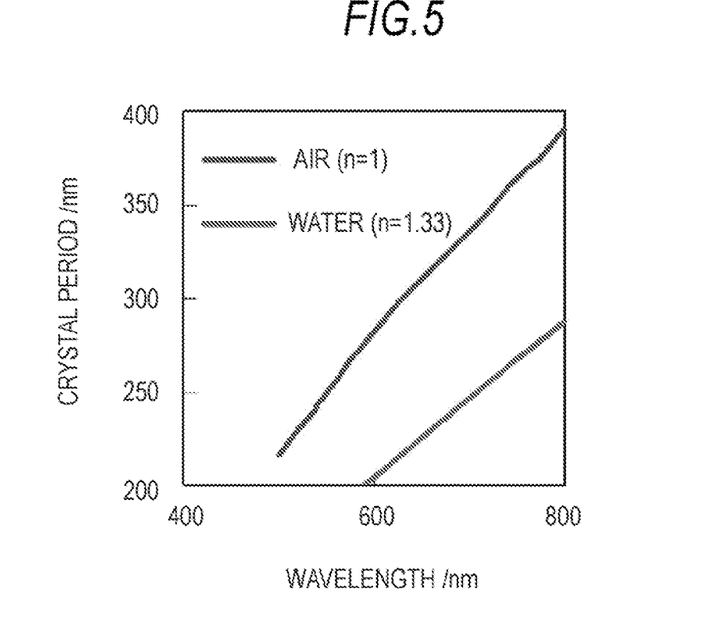
FIG. 5 is a graph showing arrangement periods (200 to 350 nm) of the plasmonic crystal satisfying the SPP dispersion relation and the Bragg reflection condition with respect to optional incident light wavelengths.

FIG. 4 shows the SPP dispersion relation and the Bragg reflection condition in the case that the arrangement period of the relief structure of the plasmonic crystal is 280 nm. The condition which satisfies the SPP dispersion relation and the Bragg reflection condition at the same time was assumed to be the condition in which the plasmonic band gap is generated. The arrangement periods of the plasmonic crystal which satisfies the condition were calculated with respect to optional incident-light wavelengths to determine the arrangement period which generates the plasmonic band gap. FIG. 5 shows arrangement periods with respect to the incident light wavelengths calculated in the arrangement periods 200 to 350 nm.

Example 2

2. Verification of the Arrangement Period of the Plasmonic Crystal which Generates the Plasmonic Band Gap with Respect to an Optional Incident Wavelength Concerning the arrangement period of the plasmonic crystal determined in Example 1, the plasmonic band gap was actually measured and the assumption was verified.
1. Actual Measurement Using White Light The plasmonic band gap was actually measured by using plasmonic crystals in which relief structures having arrangement periods of 180 to 340 nm were formed under the condition that the surface dielectric layer is air (n=1) and that wavelengths are 347 to 784 nm. The relief structures of the plasmonic crystals were formed in increments of 10 nm in the range of 180 nm to 340 nm.

Figure 6:
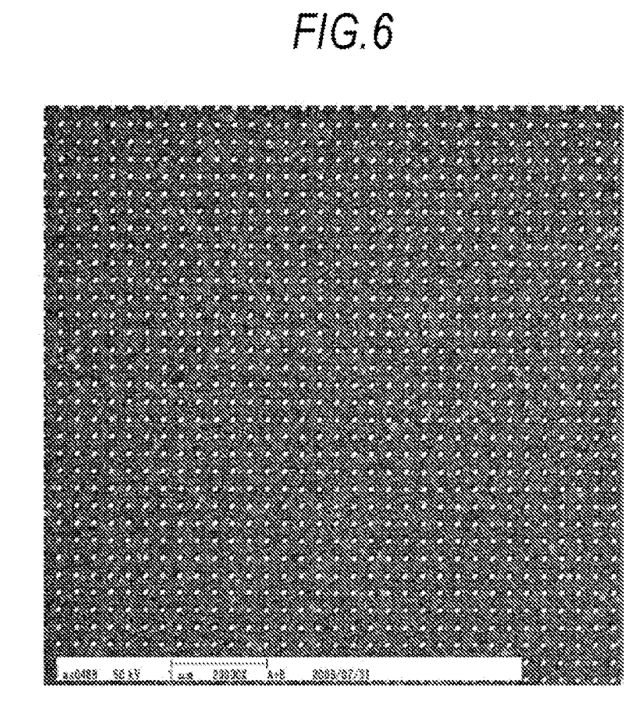
FIG. 6 is a picture substituting as a drawing, which is an electron microscopic picture of the plasmonic crystal in which the relief structure having the arrangement period 180 nm is formed.

On a BK7 substrate having 0.7 mm in thickness, Au was deposited in a thickness of 45 nm, sandwiching Cr of 1 nm therebetween as an adhesive layer. The relief structure was drawn on the surface of gold, applying PMMA as a resist by using an EB aligner ELS-7500. After development, Au was deposited in a thickness of 30 nm and the PMMA was lifted off. FIG. 6 shows an electron microscopic picture of the plasmonic crystal in which the relief structure was formed with an arrangement period 180 nm.

Figure 7:
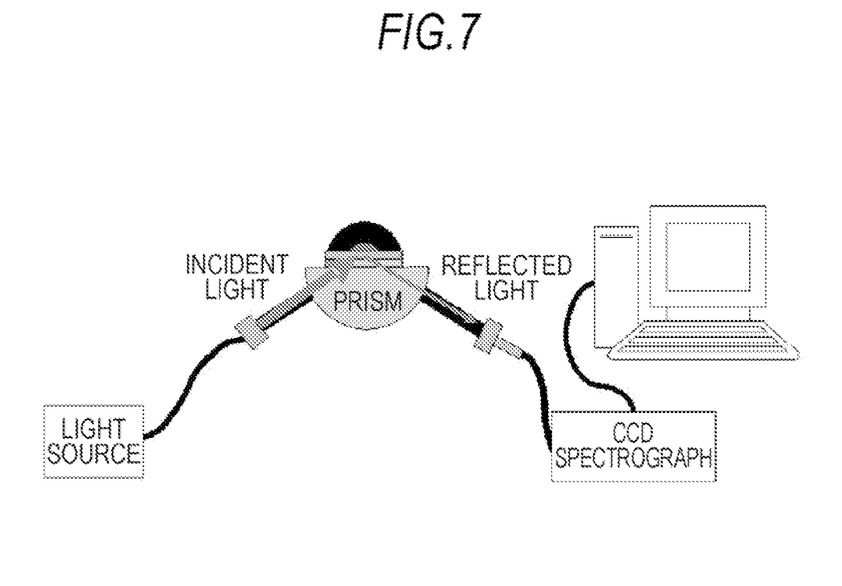
FIG. 7 is a view showing the outline of an experimental setup used in Example 2.

The substrate on which the plasmonic crystal was formed was placed on a bottom of a semicylinder-shaped prism made of BK7 through a refractive liquid. A tungsten lamp was used as a light source, light coupled to a fiber was incident from the prism side, and reflected light was lead to a CCD spectrograph by using the fiber to obtain a spectrum. FIG. 7 shows the outline of an experimental setup.

The SPP dispersion relation and the plasmonic band gap were measured by measuring reflected-light spectra while scanning with incident angles of incident light at intervals of 0.2 degrees from 41 degrees to 50 degrees.

Figure 8:
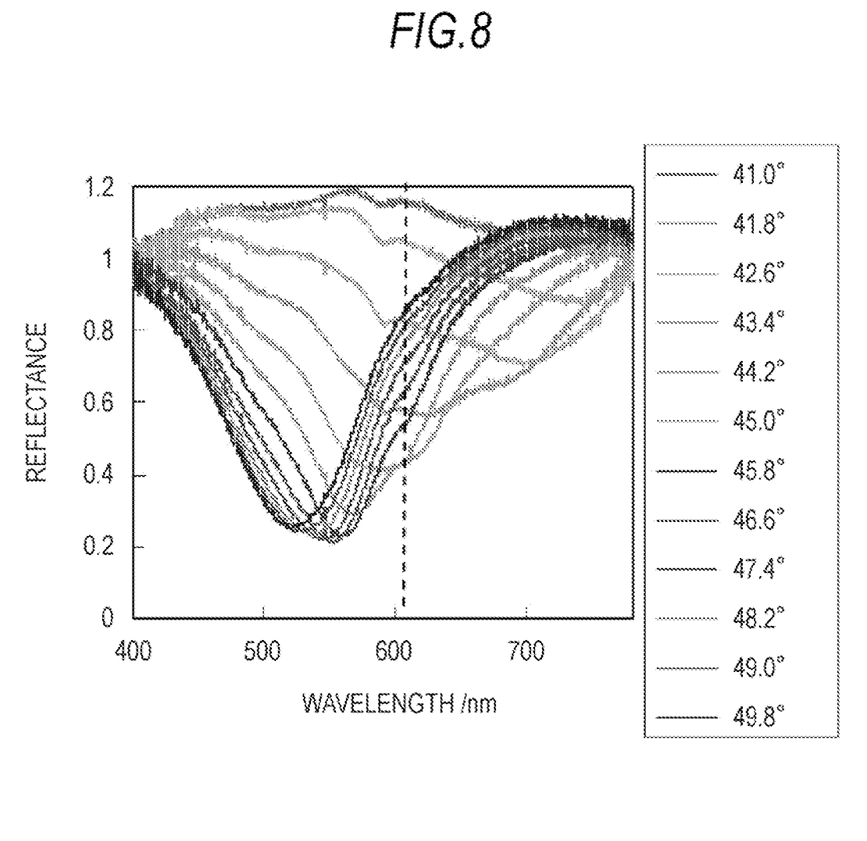
FIG. 8 is a graph showing results obtained by measuring reflected-light spectra at respective incident angles in the plasmonic crystal in which the relief structure having the arrangement period 280 nm is formed.

FIG. 8 shows results obtained by measuring reflected-light spectra at respective incident angles in the plasmonic crystal in which the relief structure having the arrangement period 280 nm was formed. The drawing shows results in which standardization was performed in the reflected-light spectrum at the incident angle of 40 degrees. In the drawing, a dotted line shows a wavelength incident light predicted from the relation between the incident wavelength and the arrangement period determined in Example 1, indicating the incident light wavelength which generates the plasmonic band gap in the plasmonic crystal of the arrangement period 280 nm.

As shown in FIG. 8, a second peak appears in the vicinity of 595 nm in addition to the main peak in the low-angle side, and a peak appears in the vicinity of 610 nm in the high-angle side. These peaks do not appear in the gold flat substrate in which the relief structure is not formed, and it can be considered as peak split due to the plasmonid band gap. The wavelength in which the plasmonic band gap appears corresponds to the wavelength of incident light predicted from the relation between the incident wavelength and the arrangement period determined in Example 1.

FIG. 9A to FIG. 9D show the SPP dispersion relations obtained by performing actual measurement of the plasmonic band gap in the plasmonic crystals in which the relief structures having arrangement periods 280, 300, 320 and 340 nm were formed in the same manner. FIG. 9A to FIG. 9D show the SPP dispersion relations of the plasmonic crystals in which the relief structures having arrangement periods 280, 300, 320 and 340 nm were formed.

Figure 9A:
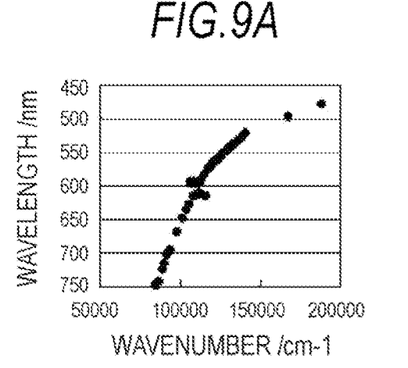
FIG. 9A to FIG. 9D show SPP dispersion relations obtained by performing actual measurement of the plasmonic band gap in the plasmonic crystals in which the relief structures having arrangement periods 280, 300, 320 and 340 nm are formed.
Figure 9B:
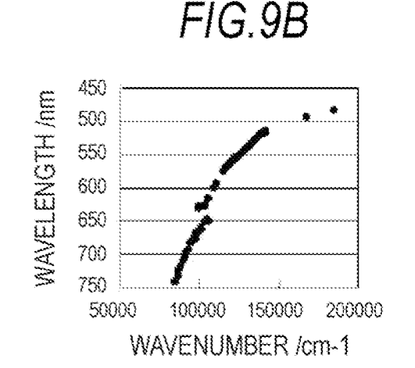
Figure 9C:
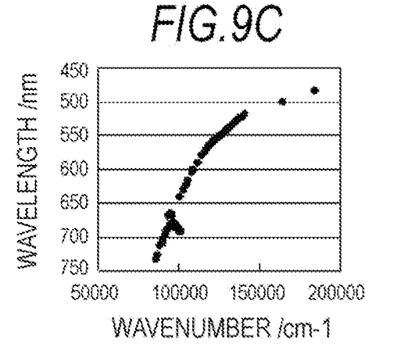
Figure 9D:
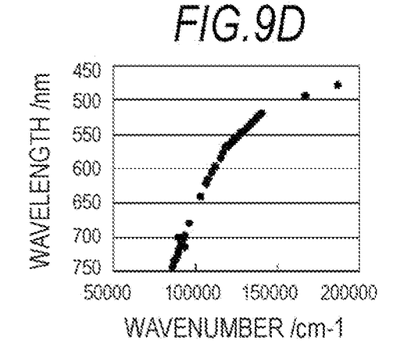

In the plasmonic crystal of FIG. 9A in which the relief structure of the arrangement period 300 nm was formed, the peak split by the plasmonic band gap can be confirmed from the vicinity of 595 nm to the vicinity of 610 nm.

In Table 1, energies of plasmonic band gap obtained by the plasmonic crystals having respective arrangement periods are shown.

TABLE 1

| Crystal period/nm | Upper end of BG/nm | Width of BG/nm | Upper end of BG/eV | Width of BG/eV |
|---|---|---|---|---|
| 340 | 703 | 9 | 1.76 | 0.022 |
| 320 | 669 | 9 | 1.85 | 0.025 |
| 300 | 630 | 19 | 1.97 | 0.058 |
| 280 | 594 | 17 | 2.08 | 0.058 |

Figure 10:
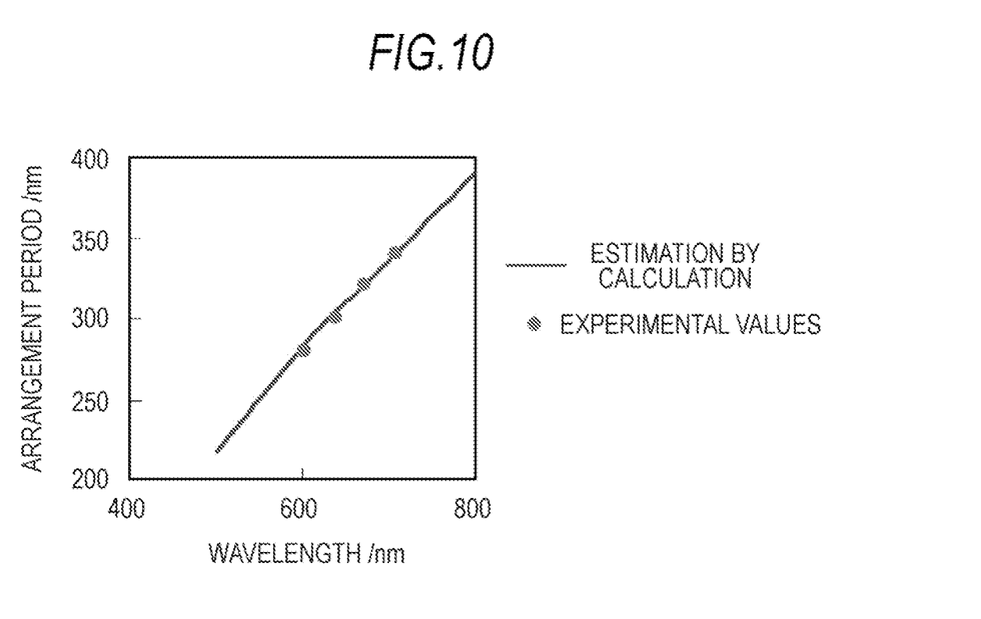
FIG. 10 is a graph showing results in which predicted values from the relation between the incident wavelength and the arrangement period determined in Example 1 are compared with actual measurement values in Example 2 with respect to energies of the plasmonic band gap obtained by the plasmonic crystals having arrangement periods 280, 300, 320 and 340 nm.

Furthermore, FIG. 10 shows results in which predicted values from the relation between the incident wavelength and the arrangement period determined in Example 1 are compared with actual measurement values in the present example with respect to energies of the plasmonic band gap obtained by the plasmonic crystals of respective arrangement periods.

From FIG. 10, it is confirmed that the prediction values and the actual measurement values of energies in the plasmonic band gap are exactly matched concerning the plasmonic crystals of respective arrangement periods. According to the results, it is possible to confirm that prediction concerning the band bap energy of the plasmonic crystal by theoretical calculation is effective.

2. Actual Measurement of SPR in the Vicinity of the Plasmonic Hand Gap End

According to the theoretical prediction based on the relation between the incident wavelength and the arrangement period determined in Example 1, it is possible to form the plasmonic crystal in which energy of the incident wave (single wavelength) corresponds to the plasmonic band gap end. In the embodiment, the behavior of the SPR curve in the vicinity of the plasmonic gap end was actually measured.

On the condition that permittivity of the surface dielectric layer n=1.33 (purified water), the arrangement period of the plasmonic crystal with respect to an incident wave wavelength 770 nm was predicted as 275 nm. The SPR measurement was performed by using the plasmonic crystals in which the relief structures having the arrangement periods of 250 nm, 260 nm, 270 nm, 280 nm and 290 nm were formed. The SPR measurement was performed by bonding a micro duct made of PDMS on a plasmonic crystal chip with purified water flowing on the plasmonic crystal. As a measuring device, the SPR sensor manufactured by Fluidware Technologies Inc. was used.

Figure 11:
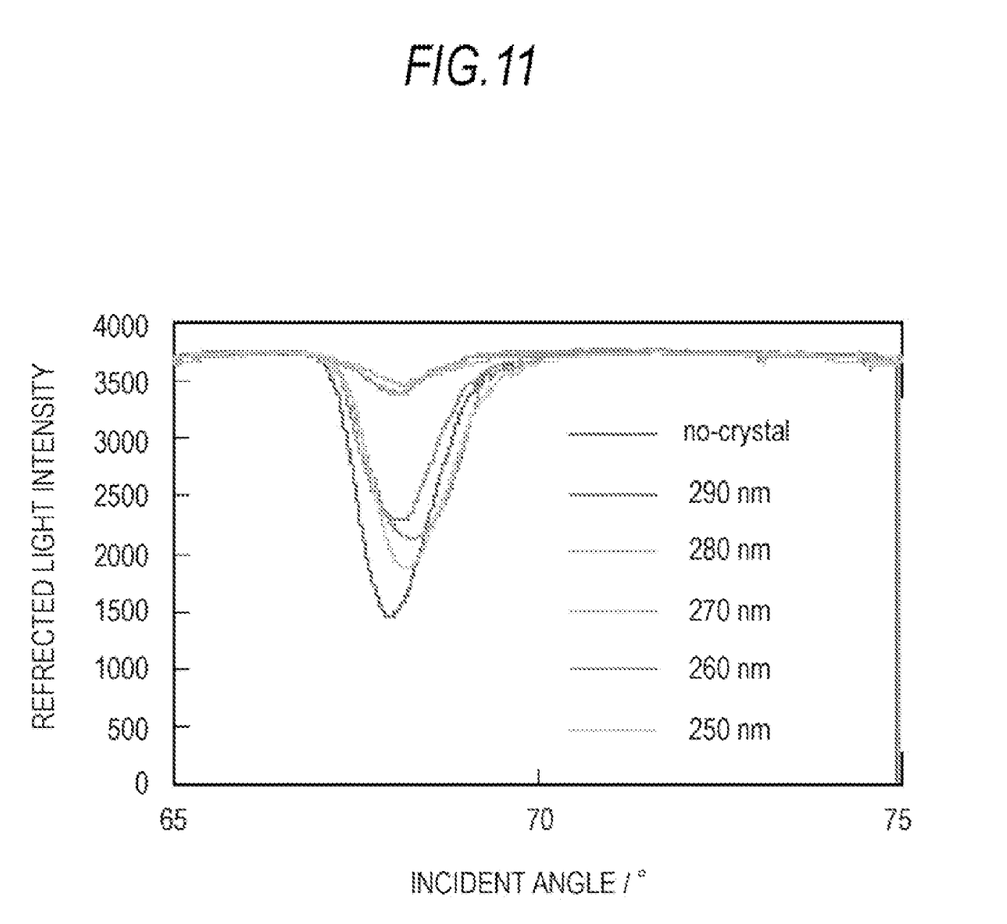
FIG. 11 is a graph showing SPR curves obtained by performing SPR measurement using the plasmonic crystals in which the relief structures having arrangement periods 250, 260, 270, 280 and 290 nm are formed.

FIG. 11 shows obtained SPR curves. The decrease of peak intensity is observed in plasmonic crystals of arrangement periods of 270 nm and 280 nm including the predicted value 275 nm therebetween. It can be considered that this is because the incident wave having the wavelength 770 nm is prohibited from propagating in the plasmonic crystal and light energy is not absorbed in the gold thin film due to the existence of the plasmonic band gap. According to the above results, it can be considered that the plasmonic band gap can be obtained by angular scanning (wavelength fixed).

As described above, in Examples 1 and 2, first, in order to use the plasmonic band gap under the optional incident wavelength condition, the condition in which the plasmonic band gap is generated was predicted from conditions in which the SPR is generated as well as in which the SPP is Bragg-reflected. Then, the plasmonic crystal satisfying the conditions was actually formed in the SPR sensor of the Kretschmann configuration to perform verification. As a result, the plasmonic band gap can be obtained in the angular scanning SPR sensor using monochromatic light by controlling the wavelength in which the band gap appears.

The design method of the plasmonic crystal according to the embodiment can be effectively used for allowing the SPR sensor to be highly sensitive. The plasmonic crystal obtained by the design method can be also used for the plasmonic band gap laser and minute lithography of photoresist.

It should be understood by those skilled in the art that various modifications, combinations, sub-combinations and alterations may occur depending on design requirements and other factors insofar as they are within the scope of the appended claims or the equivalents thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of manufacturing a plasmonic crystal, the method comprising:

forming a plasmonic crystal on a metal layer at an interface between a dielectric layer and a surface of the metal layer, an arrangement period of the plasmonic crystal is in accordance with a dispersion relation of a surface plasmon polariton at the interface and a Bragg reflection condition of the surface plasmon polariton shown in a following formula (1):

$$2 \times k_{spp} = \frac{2\pi}{\Lambda} \quad (1)$$

wherein $K_{spp}$ is a wavenumber of the surface plasmon polariton (SPP), and $\Lambda$ is the arrangement period, wherein the plasmonic crystal has a plasmonic band gap end in a frequency which corresponds to an incident-light frequency.

2. The method of manufacturing the plasmonic crystal according to claim 1, further comprising determining the arrangement period in accordance with the dispersion relation and the Bragg reflection condition under an incident-light frequency condition and a dielectric permittivity condition.

3. The method of manufacturing the plasmonic crystal according to claim 2, wherein the arrangement period is determined in accordance with the dispersion relation and the Bragg reflection condition in a surface plasmon resonance Kretschmann configuration including a dielectric, a metal and a prism.

4. A method of enabling manufacturing a surface plasmon resonance sensor, the method comprising:

forming a plasmonic crystal on a metal layer at an interface between a dielectric layer and a surface of the metal layer, an arrangement period of the plasmonic crystal is in accordance with a dispersion relation of a surface plasmon polariton at the interface and a Bragg reflection condition of the surface plasmon polariton shown in a following formula (1):

$$2 \times k_{spp} = \frac{2\pi}{\Lambda} \quad (1)$$

wherein $K_{spp}$ is a wavenumber of the surface plasmon polariton (SPP), and $\Lambda$ is the arrangement period, wherein the plasmonic crystal has a plasmonic band gap end in a frequency which corresponds to an incident-light frequency.

5. A method of enhancing light emitting intensity of dye comprising:

forming a plasmonic crystal on a metal layer at an interface between a dielectric layer and a surface of the metal layer, an arrangement period of the plasmonic crystal is in accordance with a dispersion relation of a surface plasmon polariton at the interface and a Bragg reflection condition of the surface plasmon polariton shown in a following formula (1):

$$2 \times k_{spp} = \frac{2\pi}{\Lambda} \qquad (1)$$

wherein $K_{spp}$ is a wavenumber of the surface plasmon polariton (SPP), and $\Lambda$ is the arrangement period, wherein the plasmonic crystal has a plasmonic band gap end in a frequency which corresponds to an incident-light frequency; and depositing dye thin films on the plasmonic crystal.

6. The method according to claim 1, wherein the dispersion relation of the surface plasmon polariton is determined by:

calculating a reflection light intensity in a three-layer system of the dielectric layer, the metal layer, and a prism by using Fresnel equations and equations of multiple wave interference;

calculating a surface plasmon resonance curve in the incident-light wavelength and dielectric conditions; and plotting and angle of a dip in the incident-light wavelength to obtain the dispersion relation of the surface plasmon polariton.

7. The method according to claim 1, wherein the wavenumber of the SPP is the same as the wavenumber of the interface between the dielectric layer and the metal layer.

8. The method according to claim 1, wherein the dielectric layer is air or purified water.

9. The method according to claim 1, wherein the arrangement period of the plasmonic crystal ranges from 180 to 340 nm.

10. The method according to claim 1, wherein an incident-light angle relative to the surface of the metal layer ranges from 41 to 50 degrees.

* * * * *